United States Patent [19]

Choy

[11] Patent Number: 5,762,073
[45] Date of Patent: Jun. 9, 1998

[54] METHOD AND DEVICE FOR POSITIONING A PATIENT FOR THE DIAGNOSIS OF HERNIATED LUMBAR DISC DISEASE

[76] Inventor: Daniel Shu Jen Choy, 300 E. 74th St., New York, N.Y. 10021

[21] Appl. No.: 760,503

[22] Filed: Dec. 5, 1996

[51] Int. Cl.$^6$ ........................................... A61F 5/37
[52] U.S. Cl. ...................... 128/846; 128/869; 128/870; 5/630
[58] Field of Search ...................... 128/845, 846, 128/869, 870, 782; 5/630–636, 625

[56] References Cited

U.S. PATENT DOCUMENTS

| | | | |
|---|---|---|---|
| 3,783,863 | 1/1974 | Kliever | 128/870 |
| 3,851,644 | 12/1974 | Slagle | 128/870 |
| 4,799,497 | 1/1989 | Riley | 128/782 |
| 4,956,885 | 9/1990 | Alich | 5/630 |

*Primary Examiner*—Michael A. Brown
*Attorney, Agent, or Firm*—Schweitzer Cornman Gross & Bondell LLP

[57] ABSTRACT

A method and apparatus for positioning a patient for the diagnosis of herniated lumbar disc disease permits the generation of increased intra-disc pressure which may serve to stimulate or accentuate abnormalities which can be diagnosed through MRI imaging. The apparatus consists of a frame in which a patient lies in a supine position. The frame allows the generation of muscular forces which are transmitted to the lumbar spine area. The patient is then positioned within an MRI imaging apparatus and subjected to MRI imaging while the muscular forces are maintained. The frame may preferably include a footboard and shoulder restraints positioned as to require the patient to slightly bend the knees. Extension of the legs generates the required forces.

5 Claims, 1 Drawing Sheet

METHOD AND DEVICE FOR POSITIONING A PATIENT FOR THE DIAGNOSIS OF HERNIATED LUMBAR DISC DISEASE

The present invention relates to a method intended to be used in conjunction with the diagnosis of herniated lumbar disc disease, particularly in humans, and to an apparatus which allows the methodology to be carried out.

BACKGROUND OF THE INVENTION

The human spinal or vertebral column consists of a plurality of separate vertebrae joined to each other to permit forward, backward and sideways movement of the column. At the lower end of the spinal column are the lumbar vertebrae which support the small of the back. Above the lumbar vertebrae are the thoracic vertebrae, which lie behind the thoracic or chest cavity. The uppermost cervical vertebrae define the skeletal framework of the neck. The vertebrae are separated and supported against each other by cartilaginous elements or discs, and are held together by ligaments. The discs are subject to deterioration and disease, often creating significant pain.

Studies have shown that the intra-disc pressure in the lumbar spine while in a supine position is in the neighborhood of 50 Kpa, while pressures while in the sitting position average between 150 and 200 Kpa. These correspond roughly to pressures of 7.5 and 30 psi. The observation that patients with herniated lumbar disc disease are often least comfortable in the sitting position may be at least partially due to such pressure differences.

Magnetic Resonance Imaging (MRI) techniques are often used in the diagnosis of lumbar disc disease. Experience has shown, however, that: it is not uncommon to find a dissociation between the severity of the patient's clinical symptoms and evidence of disease shown through MRI findings. This dissociation can be in part explained by the general inability of conventional MRI diagnosis systems to allow the patient to be imaged when placed into a variety of positions, including the sitting position, to vary the intra-discal pressures and alignment of the vertebrae. The supine position, in which all MRIs of the lumbosacral spine are performed, is associated with the lowest (50 Kpa) intradiscal pressure, and is thus not a good position to provoke disc herniation, and is thus far from the optimal position for effective disc herniation diagnosis. It has been shown, for example, that an L5-S1 protrusion was noticeably augmented when the patient was in the sitting position.

It is accordingly a purpose of the present invention to provide a method and apparatus for the positioning of a patient for MRI imaging in conjunction with conventional MRI imaging units which allows the spine to be placed in an orientation which may assist in the identification of diseased areas by increasing intradiscal pressure to approximate that generated in the sitting position.

It is a further purpose of the present invention to provide a method and apparatus to allow a patient to be oriented for MRI imaging in a manner which increases the intra-discal pressure in the lumbar spinal region during the imaging process.

It is still a further purpose of the present invention to provide a method and apparatus which may be utilized in connection with MRI imaging devices of conventional construction for enhanced spinal imaging procedures and which do not compromise or affect the accuracy or operation of the MRI imaging device.

BRIEF SUMMARY OF THE INVENTION

In accordance with the foregoing and other objects and purposes, an apparatus of the present invention is a non-imaging frame adapted for us in connection with an MRI imaging device which accommodates the human body in a manner which allows a compressive load to be placed upon the lumbar spine during MRI imaging. The apparatus includes longitudinal restraint means against which the patient exerts a muscular force, said force compressing the spine in a manner which simulates the forces applied thereto during sitting. The restraints may be in the form of shoulder supports and a foot board.

In accordance with the method of the present invention, the patient is positioned within an apparatus which allows the patient to exert muscular forces which correspond to the forces placed on the lumbar spine while sitting while remaining in a fixed, preferably supine position. The apparatus comprises a frame with a footboard and shoulder restraints, which has been adjusted so that the distance between the footboard and shoulder restraints is somewhat less than the normal distance. The patent can only fit in this configuration with the knees flexed. The muscular forces employed are those to straighten the knees. On straightening both knees, compression is exerted on the lumbar spine, thus increasing intradiscal pressure. The patient is then positioned for an MRI imaging of the region of interest. the patient is then directed to exert the muscular forces, and an imaging procedure of the region while such forces are exerted is performed.

BRIEF DESCRIPTION OF THE DRAWINGS

A fuller understanding of the present invention will be accomplished upon consideration of the following description of preferred but nonetheless illustrative embodiments thereof when taken in conjunction with the annexed drawings, wherein.

DETAILED DESCRIPTION OF THE INVENTION

Figure 1:
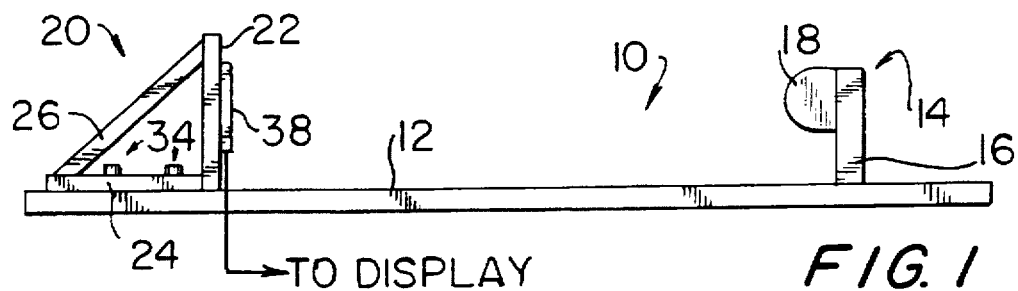
FIG. 1 is an elevation view of a patient positioning apparatus constructed in accordance with the present invention.
Figure 2:
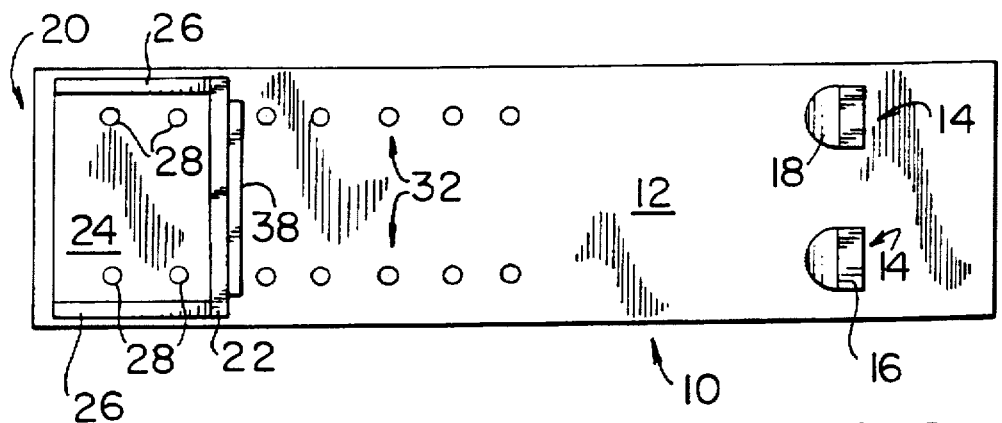
FIG. 2 is a top plan view of the apparatus.

Referring to FIGS. 1 and 2, a positioning apparatus 10 constructed in accordance with the present invention may preferably comprise a base or frame 12 which may be of rectangular shape as shown in plan. While shown in the Figures as a solid structural member, other constructions may be employed, such as an open latticework, a rail-type construction or the like. The primary requirements of the frame is that it comfortably support a supine patient, that it be constructed of a material that will not cause false or interfering images during MRI scanning, and that it be dimensioned to fit within the imaging area of an MRI apparatus. Wood and plastic structures are able to meet the requirements.

Figure 3:
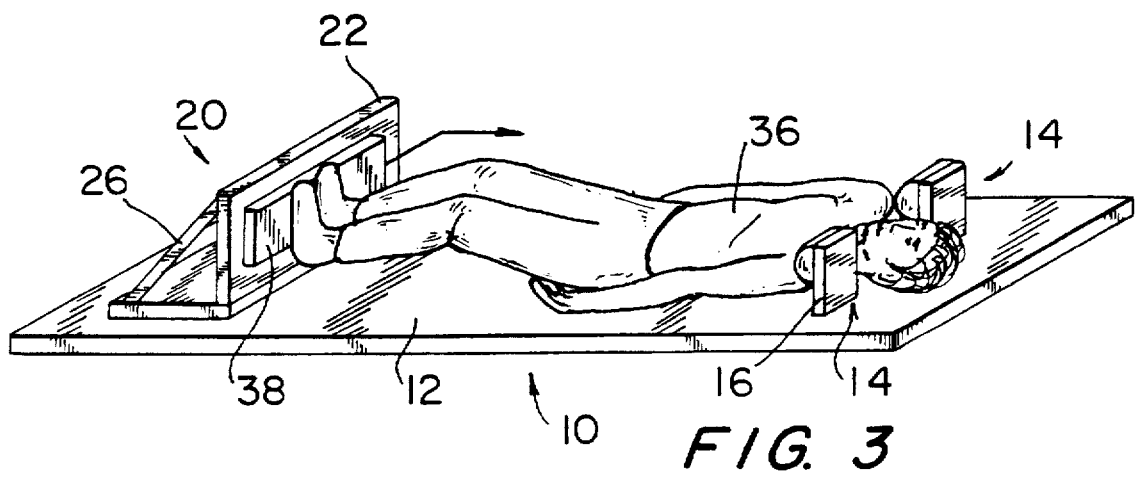
FIG. 3 is a perspective view of the apparatus showing the orientation of a patient placed thereon.

Mounted to the frame and spaced from each other are first and second longitudinal restraint means for maintaining a patient in a motion-free state while the patient exerts the desired muscular force. The first longitudinal restraint means may take the form of a pair of spaced shoulder supports 14, mounted at a first end of the frame. Each of the shoulder supports may preferably include an upwardly-projecting post 16 to which a cushion 18 is affixed. The cushions are oriented such that a patient, lying on the frame as shown in FIG. 3, bears against the cushions as a longitudinal muscular force along the length of the frame is applied against the shoulder supports. The shoulder supports are transversely spaced sufficient to allow the head and neck of the patient to fit comfortably between them.

The second longitudinal restraint means may comprise movable foot sled 20 intended to be positioned at the second end of the frame 12. The sled includes a vertically-extending footboard 22 mounted to a horizontal base 26 and braced by diagonal struts 26. The sled is selectively positioned upon the frame by aligning the pairs of bores 28, 30 in the sled base with selected pairs of corresponding positioning bores 32 in the frame. Pins 34 are inserted into the aligned bores to position the foot sled 20 in the desired lateral position along the length of the apparatus frame. Both the shoulder supports 14, foot sled 20, and the pins 34 are of sufficiently rigid construction to withstand the forces to be placed upon them and, like the frame 12, are constructed of materials which will not affect or distort the imaging process.

As depicted in FIG. 3, a patient 36 lies supine on the apparatus frame 12, his or her shoulders being supported by the shoulder supports 14 and his or her feet placed against the footboard 22 with the knees slightly bent. The position of the footboard may be adjusted as required to provide the appropriate positioning thereof. Typically, the distance between the footboard and shoulder restraint is about three inches less than that of the normal shoulder height. Once so positioned the patient is directed to attempt to extend or straighten his or her legs upon receipt of the instruction to do so. Such attempted extension, restrained by the shoulder supports and footboard, applies a compressive force to the spinal column, as the body is maintained essentially motionless by the combination of the shoulder supports and the foot sled. With the patient so directed, the apparatus and patient are placed in the appropriate position within the MRI unit to allow imaging of the spinal area to be performed. Properly oriented, the patient is instructed to extend the legs and maintain the extension until instructed to relax. The MRI scan is performed while the extension is maintained. The level of force applied by the patient may depend both on the initial degree of leg flexure and subsequent extension, as well as the muscular effort exerted. The patient may be instructed to exert sufficient force to develop pain in the affected region, or may be instructed in more general terms to merely attempt to straighten the legs. Alternatively, a force measuring device, such as a transducer 38, may be mounted to the footboard 22 and connected to a remote display apparatus to provide a more quantitative measure of the force. This will also allow the force to be monitored during the duration of a scan to insure consistency and to allow suitable instructions to be provided to the patient. After the scan is completed, the patient may then be instructed to relax.

By use of the method and apparatus of the present invention a simulation of the effects of sitting and the like upon the spine may be performed while allowing the patient to be maintained in a supine position required for conventional MRI evaluation. It thus provides for a further and alternative means for investigating and evaluating possible spinal injury, which injuries may be difficult to identify and locate when MRI analysis is performed with the spinal column being in an otherwise uncompressed state.

I claim:

1. A method of performing an MRI analysis upon the spine of a patient, comprising the steps of:

locating the patient in a positioning apparatus having first and second restraint means located apart from each other a distance whereby the patient may be positioned therebetween in a manner to apply a spine-compressing force against said restraint means;

positioning said positioning apparatus with the patient within the diagnosis area of an MRI apparatus;

causing said patient to exert a spine-compressing force against said restraint means and performing an MRI analysis of the patient while said force is maintained.

2. The method of claim 1, wherein said locating step comprises locating the patient between a pair of shoulder supports and a footboard.

3. The method of claim 2, wherein said locating step further comprises orienting the patient in a supine position between said shoulder supports and said footboard.

4. The method of claim 3, wherein said locating step further comprises locating the patient in contact with said shoulder supports and said foot board with the patient's legs bent.

5. The method of claim 1 further comprising the step of monitoring the force applied by the patient against said restraint means.

* * * * *